United States Patent
Sohal et al.

(10) Patent No.: US 6,715,917 B1
(45) Date of Patent: Apr. 6, 2004

(54) OVERHANG DESIGN FOR OPTIMAL COUNTERBALANCE AND SYSTEM COMPACTION IN A C-ARM X-RAY APPARATUS

(75) Inventors: Ratanjit Singh Sohal, Punjab (IN); Amol Gupta, Karnataka (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 26 days.

(21) Appl. No.: 10/243,134

(22) Filed: Sep. 13, 2002

(51) Int. Cl.[7] ................................................ H05G 1/02
(52) U.S. Cl. ...................................... 378/197; 378/198
(58) Field of Search .................................. 378/195, 196, 378/197, 198

(56) References Cited

U.S. PATENT DOCUMENTS 5,521,957 A * 5/1996 Hansen ........................ 378/198
5,583,909 A * 12/1996 Hanover ...................... 378/197
5,627,873 A * 5/1997 Hanover et al. ............ 378/197

* cited by examiner

Primary Examiner—David V. Bruce
Assistant Examiner—Hoon Song
(74) Attorney, Agent, or Firm—Joseph S. Heino; Carl B. Horton

(57) ABSTRACT

A support arm for use with a C-arm x-ray imaging machine is interposed between the yoke and the cross member of a C-arm x-ray imaging machine. The support arm is a generally rectangular structure having a first end, a second end and a central area between the first end and the second end, a generally circular pin attached to or integrally molded with the first end of the rectangular structure, said pin being set at an obtuse angle relative to the vertical, and a generally circular aperture defined within the second end of the rectangular structure. The support arm also includes a plurality of weight reducing apertures, or pockets, are defined within the support arm and the weight reducing pockets are covered with a plate to prevent contamination. The support arm reduces the overall length of the x-ray apparatus, brings the axis of rotation of the C-arm closer to the center of gravity and saves weight.

29 Claims, 4 Drawing Sheets

OVERHANG DESIGN FOR OPTIMAL COUNTERBALANCE AND SYSTEM COMPACTION IN A C-ARM X-RAY APPARATUS

BACKGROUND OF THE INVENTION

1. Field of the Invention

The present invention relates generally to the area of x-ray imaging systems and devices used with such diagnostic x-ray systems. More specifically, the present invention relates to a C-arm x-ray imaging apparatus that incorporates new and improved mechanisms for adjustment and control of the C-arm.

2. Background of the Invention

It is frequently necessary to conduct an x-ray examination of a patient without repositioning the patient. To that end, mobile C-arm x-ray diagnostic equipment, such as that shown in FIG. 1, has been developed to meet this need. Such equipment is now well known in the medical and surgical arts. The C-arm machine is especially useful in that it is small enough and mobile enough to be present in an operating or exam situation without requiring the physician to repeatedly move or requiring the patient to change positions to obtain a suitable image.

C-arm imaging machines are well known and widely used in the medical arts. Examples of their uses include bone density measurement and fluoroscopic imaging during surgical procedures. The term "C-arm" refers to the generally C-shaped member that has an x-ray source and an image receptor, or detector, mounted on opposing ends of the "C" such that x-rays emitted by the source are incident on and detected by the receptor. The source and the detector are positioned such that when, for example, a human extremity is interposed between the x-ray source and the image receptor and is thereby irradiated with x-rays, the receptor produces data representative of characteristics of the interposed extremity. The data produced is frequently displayed on a monitor and electronically saved.

The C-arm portion of the machine is normally mounted such that it is permitted two degrees of freedom. First, the C-arm track is slidably mounted to the support member so as to be movable in relation to the support member. This permits the x-ray source and image receptor to be moved rotatably about the arc of curvature of the track in the C-arm. The C-arm support member also permits rotation of the C-arm about its axis. Often the support member is referred to as the yoke. Mobile C-arms have a third degree of freedom in that they are free to move horizontally along the floor and a fourth in that the C-arm can be raised and lowered.

Obviously, a support structure that permits rotation and movement of such a C-arm must be properly counterbalanced and constructed to withstand large torsional, tensile and compressive stresses. It is also desirable to provide a support structure that is heavy enough and that has a center of gravity low enough to avoid tipping when the C-arm and Yoke are rotated or raised, which in some cases causes a dramatic shift in the center of mass of the machine.

Notwithstanding its size and mass, the C-arm x-ray machine must be delicately positioned in order to render the image or images as are desired or required by the physician. Unfortunately, the weight of the support structure can make it difficult to position the C-arm. Therfore, t is also desirable to balance the C-arm, x-ray source, x-ray detector and yoke so that relatively little physical effort is required to move the C-arm about the orbital rotation axis and the lateral rotation axis. One manner of accomplishing this is to design the C-arm such that its center of mass is as close as possible to the orbital and lateral rotation axes.

Some C-arm designs require a center of mass that is separate from the axis of rotation. In these unbalanced designs, the user must exert significant force to rotate the apparatus. This physical exertion generally detracts from other, more significant tasks a health care provider may be undertaking. Also, unbalanced designs can be dangerous to both the operator and the patient. For example, unbalanced C-arms require much more powerful braking systems. Without an adequate braking system, the C-arm could rotate downward and strike an individual.

What is needed is a C-arm x-ray machine that has a lower rotation axis such that the axis of rotation passes through the center of gravity of the yoke and the C-arm portion of the machine. What is also needed is such a machine whereby the overall length is reduced. What is also needed is such a machine whereby sag of the C-arm portion of the machine is compensated for. What is also needed is such a machine whereby miminal impact is effected on the existing support structures of the C-arm machine so that mainframe designs can continue to be utilized notwithstanding the aforementioned improvements.

BRIEF SUMMARY OF THE INVENTION

Accordingly, it is an object of the present invention to provide a C-arm x-ray machine that is optimally balanced and requires little effort to rotate. It is yet another object of the present invention to provide such a device that requires relatively few parts and can be easily manufactured. It is also an object of this invention to reduce the overall length of the system. It is still another object of the present invention to provide such a machine whereby the rotation axis passes through the center of gravity of the yoke and the C-arm structure. It is yet another object of the present invention to reduce the overall length of the machine, reduce mass of the yoke and to compensate for sag of the C-arm portion of the machine. It is a further object of the present invention to provide such a machine whereby this alteration can be utilized with existing mainframes, or "doghouses" of current design. It is yet another object of the present invention to accomplish all of this while providing an aesthetically pleasing and aseptic device.

The device of the present invention has achieved these objects. It provides for a C-arm x-ray apparatus having a support arm between the yoke and the cross arm that reduces the space used by the x-ray apparatus by taking advantage of the space that exists underneath the cross arm. This new support arm is also designed to align the axis of rotation of the C-arm with the C-arm's center of gravity. The new support arm is also constructed so as to minimize mass and to compensate for C-arm sag by creating an angular presentation of the arm relative to the horizontal. Additional objects and advantages of the invention will be set forth in the description that follows. Other objects and advantages may be learned by practice of the invention.

DETAILED DESCRIPTION OF THE INVENTION

The following detailed description is intended to describe the preferred embodiments that are depicted in the figures. It is to be understood that changes could be made to that which is specifically described and shown that would still fall within the scope of the present invention.

Figure 2:
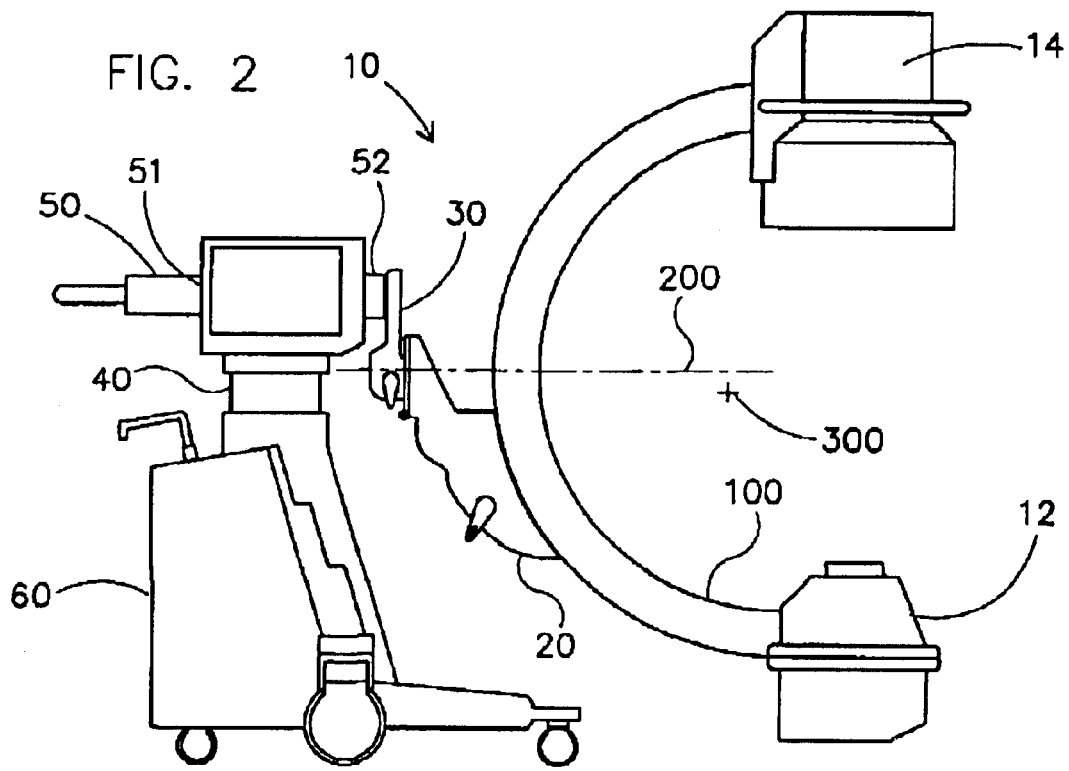
FIG. 2 is a left side elevational view of a C-arm x-ray machine constructed in accordance with the present invention.

Referring now to the drawings in detail, wherein like numbered elements refer to like elements throughout, FIG. 2 illustrates the basic components of a C-arm x-ray imaging machine constructed in accordance with the present invention. In general, the C-arm x-ray imaging machine, generally identified 10, is comprised of the following components: an x-ray source 12, an image receptor 14, an image processing system, a display and viewing system, a high voltage generator and a control unit, the latter of which is not specifically shown but contained within the "doghouse" or mainframe 60.

The x-ray source 12 preferably comprises an x-ray tube and a high-voltage generator. The high-voltage generator is preferably connected to an adjustable high-voltage power supply capable of generating approximately −70 kV to −120 kV. The x-ray source 12 is generally a scanning beam x-ray in which charged particles are scanned across a target assembly. When the system is operated, the charged particle beam strikes the target and generates x-ray photons. The x-ray photons preferably pass through a collimator and form an x-ray beam. The x-ray beam has an axis that is substantially aligned with the center of the active area of the x-ray detector 14. The x-ray beam has a vector that is defined by the axis of the x-ray beam in the direction of the x-ray detector 14 assembly.

The imaging object is typically the patient or some extremity of the patient. X-rays that have passed through the patient are detected and later processed for some form of interpretation.

The detection and recording system is generally comprised of the image receptor 14. The image receptor 14 captures the x-ray photons scanned across the imaging object and converts them to electrical signals. The impulses are then converted to digital data and either stored or fed immediately into a computer for image reconstruction. The imaging process system generally consists of a computer with a software package that reconstructs the image and displays the image on a screen and a device that provides for storage of the image.

The display system and the control unit are normally remotely operated. Thus the operator can be shielded from radiation but still perform the x-ray study. Alternatively, the entire system can be placed in an examining or operating room so that the health care provider can view images of the patient in real time.

As alluded to earlier, the mobile C-arm x-ray imaging machine, 10 includes a wheeled mainframe or support base 60. In a preferred embodiment the support base 60 is a generally rectangular upright body that may be equipped with one or more video monitors and has an upper portion or vertically extendable column 40 with an extendable cross arm 50. The extendable cross arm 50 has a first portion 51 slidably mounted within the vertically extendable column 40 and a second end 52 having an aperture 53 defined in the end of the cross arm 50. The support base 60 is important to the imaging machine 10 in that it provides a platform for the yoke 20 and the C-arm 100. Therefore, the support base 60 should have a footprint large enough such that the yoke 20 and C-arm 100 are permitted to rotate without the danger of tipping. The support base 60 must also be heavy enough to prevent tipping of the x-ray apparatus 10.

The C-arm 100 is a generally semicircular apparatus that is held in a rotational sliding position by a series of bearings on second end of the yoke 20. The first end of the C-arm 100 has an x-ray source 14 and the second end 12 of the C-arm 100 has an image receptor 14. The C-arm 100 maintains the x-ray source 12 and an image receptor 14 in diametrically facing positions.

The C-arm 100 is generally capable of movement in at least two degrees of freedom. The first end of the yoke 20 is permitted to rotate 360 degrees about its connection with the cabinet support. Also, the exterior of the C-arm 100 is permitted to roll along the second end of the yoke 20. Generally, the C-arm 100 is permitted to rotate orbitally around its own axis. The breadth of rotation of the C-arm 100 is limited only by the width of the yoke 20.

Figure 1:
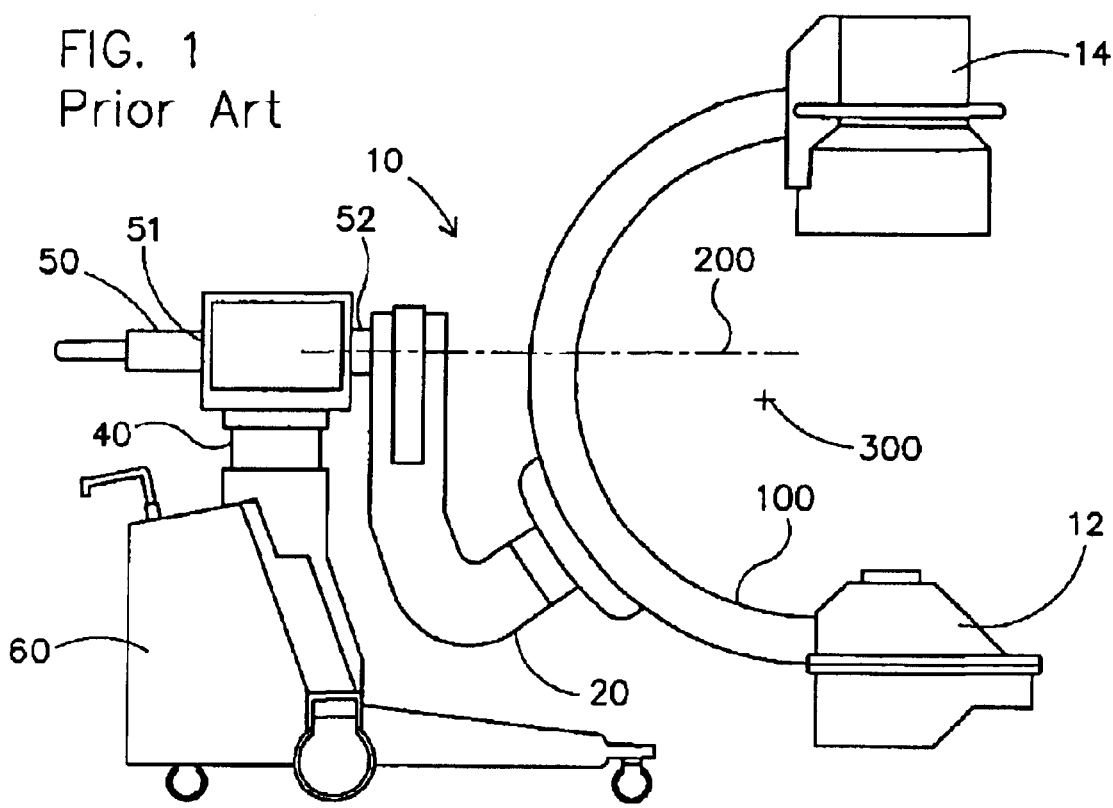
FIG. 1 is a left side elevational view of a C-arm x-ray machine known in the art.

The device of the present invention, unlike previous devices provides a support arm 30 between the yoke 20 and the support base 60. The support arm 30 is designed to lower the axis of rotation 200 such that the axis of rotation 200 coincides, or very nearly coincides with the center of gravity 300 of the C-arm 100. See FIG. 1. The closer the center of gravity 300 of the C-arm 100 to the C-arm's 100 axis of rotation 200, the smaller the force required to rotate the C-arm 100. As is shown in FIG. 1 and FIG. 2, the present invention significantly reduces the distance between the axis of rotation 200 and the center of gravity 300.

Figure 3:
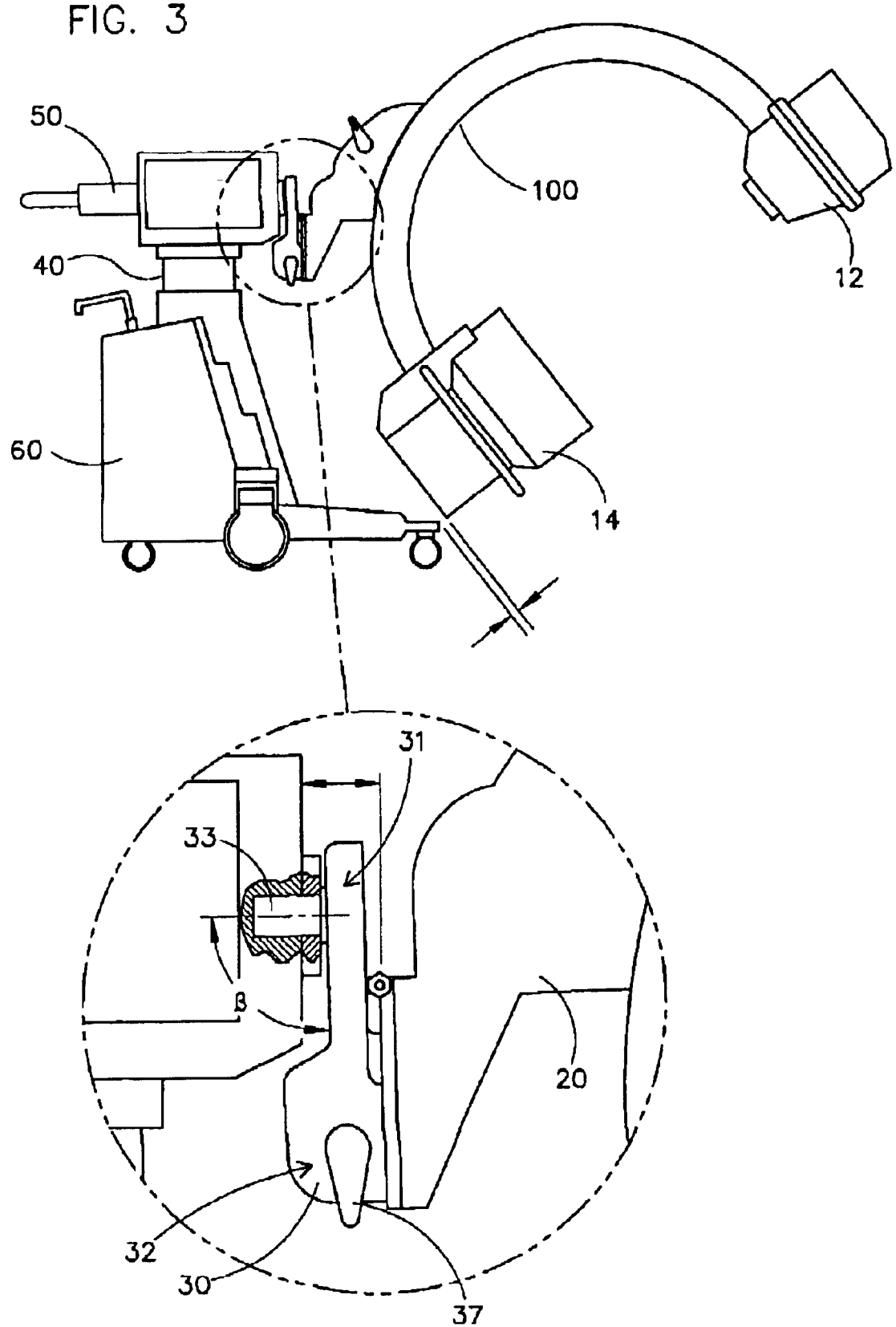
FIG. 3 is a left side elevational view of the C-arm x-ray machine shown in FIG. 2 and illustrating an inversion of the C-arm portion to demonstrate clearance of the C-arm portion with the mainframe. It also shows an enlarged view of the overhang support arm attachment in accordance with the present invention.
Figure 4:
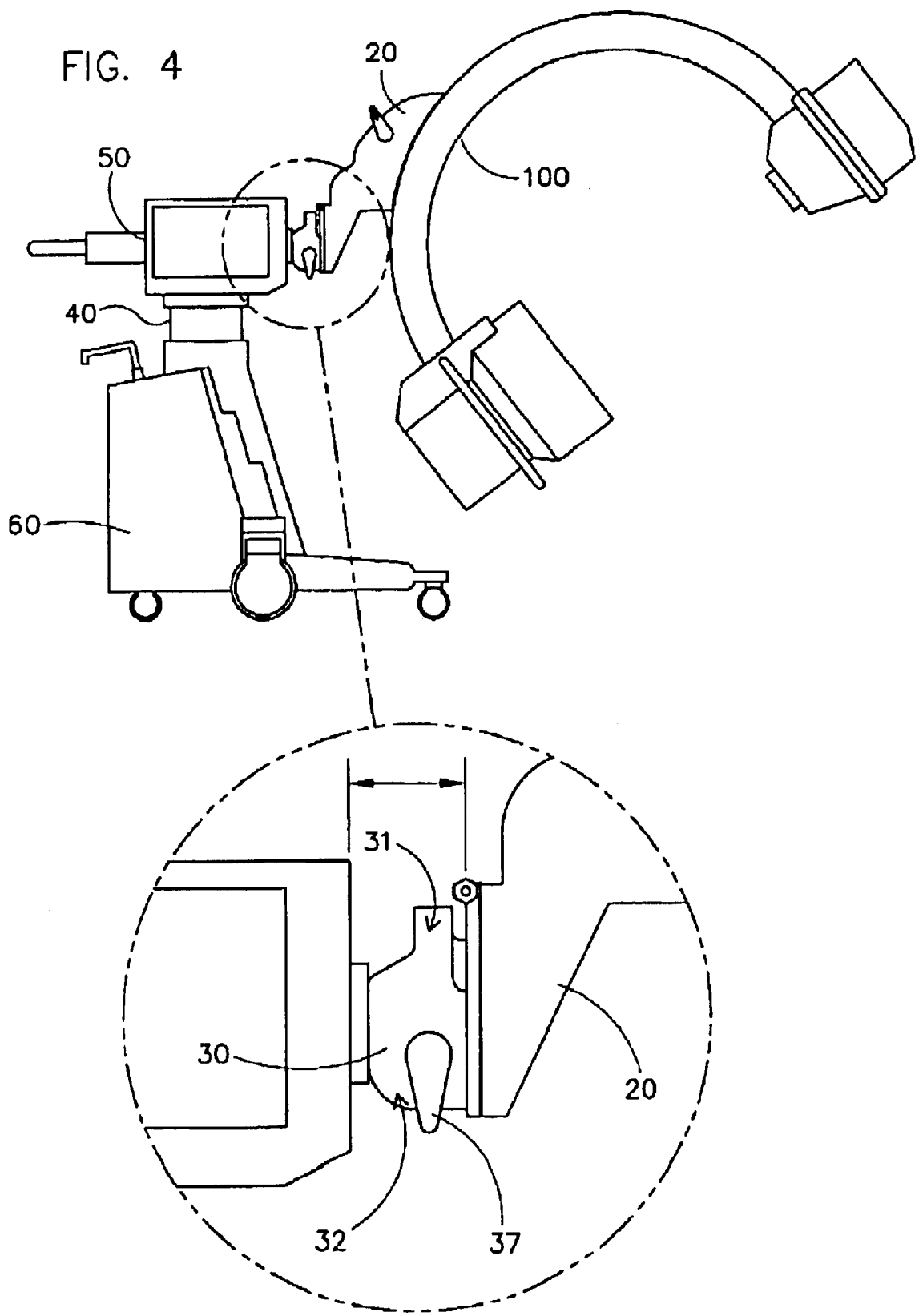
FIG. 4 is a left side elevational view of the C-arm x-ray machine shown in FIG. 3 and illustrating an alternative mounting of the overhang to show the saving on overall length of the machine. It also shows an enlarged view of the overhang support arm attachment.

Referring now to FIG. 3, it will be seen that the support arm 30 is a generally rectangular part having a first end 31 with a support pin 33 that is insertable into the second end 52 of the cross arm 50 and a thick second end 32 having an aperture 34 defined within it that accommodates the pin and steel sleeve of the yoke 20. The support pin 33 is set at an obtuse upward angle (identified in FIG. 5 as β) to compensate for the weight of the C-arm 100 and yoke 20. In the preferred embodiment, the support pin 33 is set at an angle of 91.5 degrees from the vertical, although other angles could be used.

Defined within the support arm 30 is a plurality of weight reducing pockets 35. See FIG. 5. The pockets 35 are designed to reduce the weight of the C-arm 100, which reduces the amount of effort required to rotate the C-arm 100. Before final assembly, the pockets 35 are covered with a plate 36 to prevent bacterial and other unsightly and unsanitary accumulations within the pockets 35. This provides an aesthetically pleasing and aseptic device.

The support arm 31 contains a brake mechanism with an exterior brake handle 37. The brake mechanism is either engaged or disengaged using the brake handle 37. The brake mechanism itself is used to alternately permit or prohibit rotation of the C-arm 100. In this manner, the C-arm 100 can be easily rotated into position and locked in place using the brake mechanism.

Figure 5:
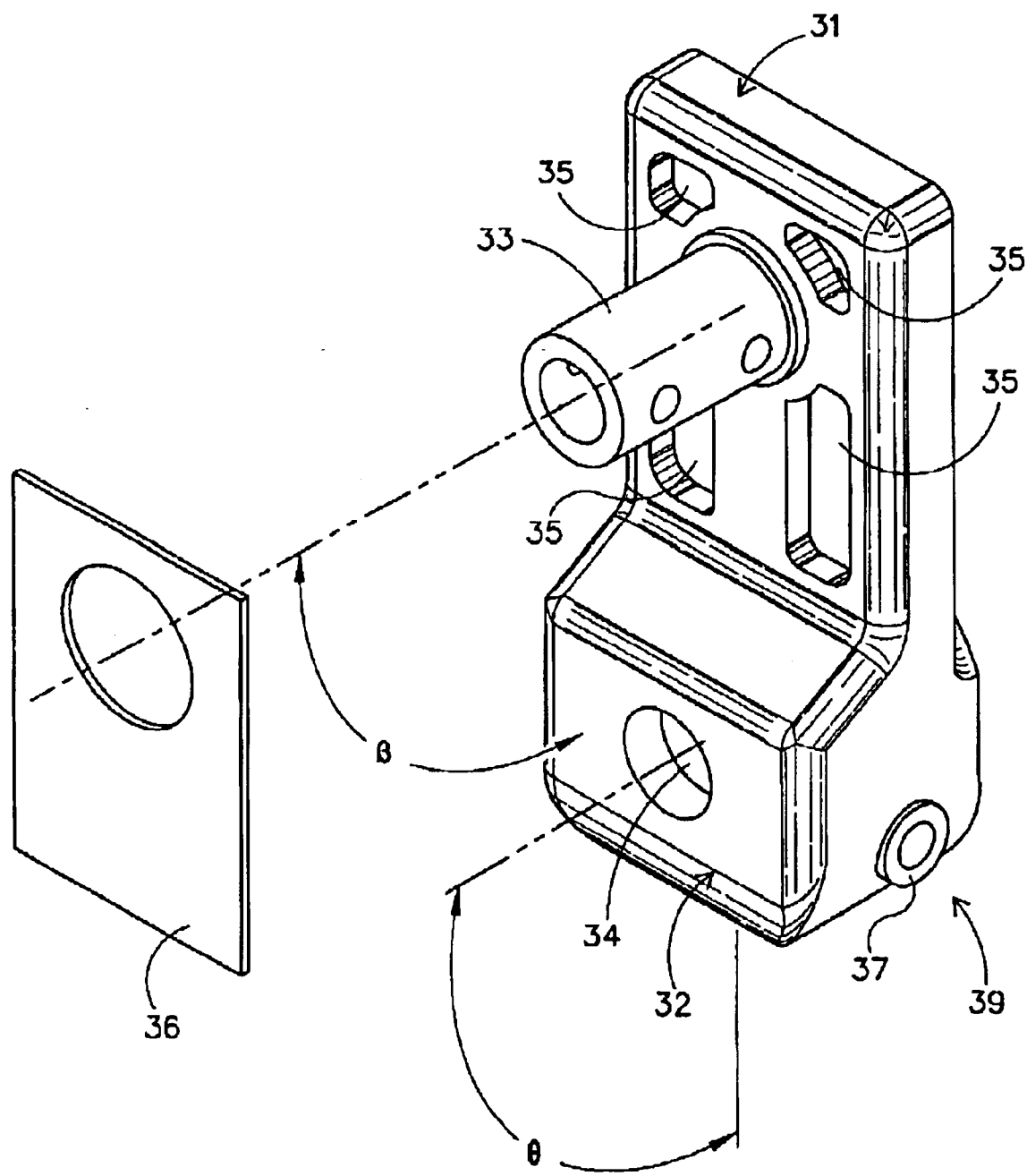
FIG. 5 is an enlarged top, rear and left side perspective view of the overhang support arm constructed in accordance with the present invention and showing the weight reduction pockets defined in it.

Unlike previous devices, the unique support arm 30 of the present invention strategically utilizes the space underneath the doghouse 60, thus reducing the overall space requirements of the C-arm x-ray machine 10. As shown in FIG. 5, the second end 32 of the support arm 30 flares outwardly to form a box-type structure 39. This box-type structure 39 accommodates the yoke aperture 34, and is a generally circular. As is best shown in FIG. 3, the support arm actually uses the space underneath the second end 52 of the cross arm 50 and is strategically placed partly underneath the vertically extendable column 40.

The redesigned support arm 30 also reduces the effort required to rotate the C-arm 100. As can best be observed in FIG. 1 (Prior Art) and FIG. 2 the axis of rotation of the C-arm 100 is significantly closer to the center of gravity of the C-arm in FIG. 2, the device of the present invention. This attribute significantly reduces the effort required to rotate the C-arm 100 and reduces the chance of patient or operator injury due to unexpected rotation of the C-arm 100.

It is to be understood that the invention is not limited to the embodiments set forth herein but that the invention may be carried out in other ways without departing from the spirit of the invention.

Parts List:

| | |
|---|---|
| 10 | C-arm x-ray imaging apparatus |
| 12 | x-ray source |
| 14 | image receptor |
| 20 | yoke |
| 30 | support arm |
| 31 | first end of the support arm |
| 32 | second end of the support arm |
| 33 | support pin on the first end of the support arm |
| 34 | aperture in the second end of the support arm |
| 35 | pockets |
| 36 | covering plate |
| 37 | support arm brake |
| 39 | box-type structure at the second end of the support arm |
| 40 | vertical column |
| 50 | cross arm |
| 51 | first end of the cross arm |
| 52 | second end of the cross arm |
| 53 | aperture defined within the second end of the cross arm |
| 60 | support base |
| 100 | C-arm |
| 200 | axis of rotation of the C-arm |
| 300 | center of gravity of the C-arm |

What is claimed is:

1. A C-arm x-ray imaging apparatus (10) comprising:

a moveable support base (60), a vertically extending column (40) attached to the support base (60), an extendable cross arm (50) having a first end (51) slidably attached to said vertically extending column (46) and a second end (52), a support arm (30) having a first end (31) attached to the second end (52) of the cross arm (50) and a second end (32), a yoke (20) having a first end attached to the second end (32) of the support arm (30) wherein the yoke (20) is permitted to rotate, said yoke (20) having a second end, a C-arm (100) attached to the second end of the yoke (20), an x-ray source (12), an image receptor (14)

wherein the image receptor (14) and the x-ray source (12) are mounted on opposing ends of the C-arm (100).

2. The imaging apparatus of claim 1 wherein the cross arm (50) has a first end (51), a second end (52), said second end (52) having an aperture (53) and said first end (31) of the support arm (30) having a pin (33) insertable within the second end (52) of the cross arm (50).

3. The imaging apparatus of claim 2 wherein the pin (33) of the support arm (30) is set at an angle slightly greater than 90 degrees from the support arm (30).

4. The imaging apparatus of claim 3 wherein the pin (33) of the support member (30) is set at an angle of 91.5 degrees from the support arm (30).

5. The imaging apparatus of claim 4 wherein the second end (32) of the support member (30) has a circular aperture (34) and the yoke (20) features a pin generally the same size and shape as the aperture (34) that fits within said aperture (34).

6. The imaging apparatus of claim 5 wherein the pin on the first end of the yoke (20) is alternatively permitted to rotate and prevented from rotating by a brake.

7. The imaging apparatus of claim 6 wherein the brake is controlled by a brake handle (37) external of the support arm (30).

8. The imaging apparatus of claim 7 wherein the support arm (30) has a plurality of apertures (35) that reduce the weight of the support arm (30).

9. The imaging apparatus of claim 8 wherein the apertures (35) in the support arm (30) are covered by a plate (36) to avoid hygiene problems.

10. A C-arm x-ray imaging apparatus (10) comprising a moveable support base (60) having a top, a bottom and a plurality of sidewalls, a vertically extending column (40) attached to the support base (60), an extendable cross arm (50) having a first end (51) slidably attached to the vertically extending column (40) and a second end (52) providing a generally circular aperture(53), a generally rectangular support arm (30) having a first end (31), a second end (32) and a middle portion, the first end (31) featuring a generally circular pin (33) insertable into the generally circular aperture (53) of the cross arm (50), middle portion and a second end (32) flared outwardly and forming a box structure (39), said box structure (39) having a generally circular aperture (34), a yoke (20) having a first end with a generally circular pin insertable within the aperture 34 at the second end 32 of the support arm 30, the yoke (20) being permitted to rotate, said yoke (20) having a second end, a C-arm (100) attached to the second end of said yoke (20), an x-ray source, an image receptor wherein the image receptor and x-ray source are mounted on opposing ends of the C-arm.

11. The imaging apparatus of claim 10 wherein the pin (33) of the support arm (30) is set at an angle slightly greater than 90 degrees from the support arm (30).

12. The imaging apparatus of claim 11 wherein the pin (33) of the support member (30) is set at an angle of 91.5 degrees from the support arm (30).

13. The imaging apparatus of claim 12 wherein the second end (32) of the support member (30) has a circular aperture (34) and the yoke (20) features a pin generally the same size and shape as the aperture (34) that fits within said aperture (34).

14. The imaging apparatus of claim 13 wherein the pin on the first end of the yoke (20) is alternatively permitted to rotate and prevented from rotating by a brake.

15. The imaging apparatus of claim 14 wherein the brake is controlled by a brake handle (37) external of the support arm (30).

16. The imaging apparatus of claim 15 wherein the support arm (30) has a plurality of apertures (35) that reduce the weight of the support arm (30).

17. The imaging apparatus of claim 16 wherein the apertures (35) in the support arm (30) are covered by a plate 36 to avoid hygiene problems.

18. The imaging apparatus of claim 17 wherein the one of the flared sides of the second end (32) of the support arm (30) extends under the cross arm (50).

19. A support arm (30) for use with a C-arm x-ray imaging apparatus (100) comprising a generally rectangular structure having a first end (31), a second end (32) and a central area between the first end (31) and the second end (32), a generally circular pin (33) attached to or integrally molded with the first end (31) of the rectangular structure, a generally circular aperture (34) defined within the second end (32) of the rectangular structure, wherein the support arm (30) is interposed between the cross arm (50) and the yoke (20) of a C-arm x-ray apparatus (10).

20. The support arm (30) of claim 19 wherein the pin (33) is set at an obtuse upward angle 9.

21. The support arm (30) of claim 20 wherein the pin (33) is set at an angle of 91.5 degrees.

22. The support arm (30) of claim 21 wherein a plurality of weight reducing apertures, or pockets (35) are defined within the support arm (30).

23. The support arm (30) of claim 22 wherein the weight reducing pockets (35) are covered with a plate (36) to improve the aesthetic appeal of the support arm (30) and to prevent accumulation of bacteria.

24. The support arm (30) of claim 23 wherein the said support arm (30) includes a brake that alternately permits and prohibits rotation of the yoke (20).

25. A support arm (30) for use with a C-arm x-ray imaging apparatus (10), said C-arm x-ray imaging apparatus (10) including a cross arm (30) and a yoke (20) and said support arm (30) being disposed between the cross arm (50) and the yoke (20), which comprises a generally rectangular structure having a first end (31), a second end (32) and a central area between the first end (31) and the second end (32), a generally circular pin (33) attached to or integrally molded with the first end (31) of the rectangular structure, said pin (33) being set at an obtuse angle relative to the vertical, and a generally circular aperture (34) defined within the second end (32) of the rectangular structure.

26. The support arm of claim 24 wherein a plurality of weight reducing apertures, or pockets (35) are defined within the support arm (30).

27. The support arm of claim 25 wherein the weight reducing pockets (35) are covered with a plate (36) to improve the aesthetic appeal of the support arm (30) and to prevent accumulation of bacteria.

28. For use with a C-arm x-ray imaging apparatus (10 ), said C-arm x-ray imaging apparatus (10) including a generally horizontal cross arm (50) and a yoke (20), a support arm (30) being disposed between the cross arm (50) and the yoke (20) comprising a generally rectangular structure having a first end (31), a second end (32) and a central area between the first end (31) and the second end (32), a generally circular pin (33) attached to or integrally molded with the first end (31) of the rectangular structure, said pin (33) being set at an obtuse angle relative to the vertical, and a generally circular aperture (34) defined within the second end (32) of the rectangular structure.

29. The support arm (30) of claim 27 wherein a plurality of weight reducing apertures, or pockets (35) are defined within the support arm (30) and the weight reducing pockets (35) are covered with a plate (36).

* * * * *